(12) United States Patent
Fleming

(10) Patent No.: US 8,479,744 B2
(45) Date of Patent: Jul. 9, 2013

(54) FIN EARPLUG

(75) Inventor: Thomas W. Fleming, San Diego, CA (US)

(73) Assignee: Sperlan Hearing Protection, LLC, San Diego, CA (US)

( * ) Notice: Subject to any disclaimer, the term of this patent is extended or adjusted under 35 U.S.C. 154(b) by 2084 days.

(21) Appl. No.: 11/144,514

(22) Filed: Jun. 3, 2005

(65) Prior Publication Data

US 2006/0272649 A1  Dec. 7, 2006

(51) Int. Cl.
*A61F 11/00* (2006.01)

(52) U.S. Cl.
USPC .......................................... 128/864; 128/867

(58) Field of Classification Search
USPC .......................................... 128/864, 865, 867
See application file for complete search history.

(56) References Cited

U.S. PATENT DOCUMENTS

| | | | |
|---|---|---|---|
| 2,487,038 A | 11/1949 | Baum | |
| D195,322 S | 5/1963 | Hill et al. | |
| 4,055,233 A | 10/1977 | Huntress | |
| D265,129 S * | 6/1982 | Leight | D24/106 |
| 4,540,063 A * | 9/1985 | Ochi et al. | 181/135 |
| 4,867,149 A | 9/1989 | Falco | |
| 5,727,566 A * | 3/1998 | Leight | 128/857 |
| 6,241,041 B1 | 6/2001 | Leight | |
| 6,408,981 B1 * | 6/2002 | Smith et al. | 181/126 |
| 6,568,394 B2 * | 5/2003 | Falco | 128/864 |
| 6,820,717 B2 * | 11/2004 | Fleming et al. | 181/135 |
| D539,415 S * | 3/2007 | Fleming | D24/106 |

* cited by examiner

*Primary Examiner* — Patricia Bianco
*Assistant Examiner* — Camtu Nguyen
(74) *Attorney, Agent, or Firm* — Conley Rose, P.C.; Kristin Jordan Harkins

(57) ABSTRACT

An earplug with a stem (22) and with fins (31-34) extending at rearward and radially-outward inclines from the stem, is constructed for comfort and for high noise blocking. The stem has a multiplicity of air pockets (60) lying in an imaginary band (62) that lies on the earplug axis (20). The band has opposite band sides (64, 66) spaced radially inward of the periphery (40) of the stem, the air pockets helping to block the passage of noise. A plurality of the fins are of constant thickness with parallel front and rear surfaces (50, 52), and with the fins being stubby with a fin thickness (T) at least 20% of the fin length (E), and with the front surface (50) of each fin being at least 20% longer than the fin length (E), all as seen in a sectional view taken along the earplug axis (20). Stem peripheral parts (80) that lie between adjacent fins, extend continuously at rearward and radially inward inclines of more than 15°.

7 Claims, 2 Drawing Sheets

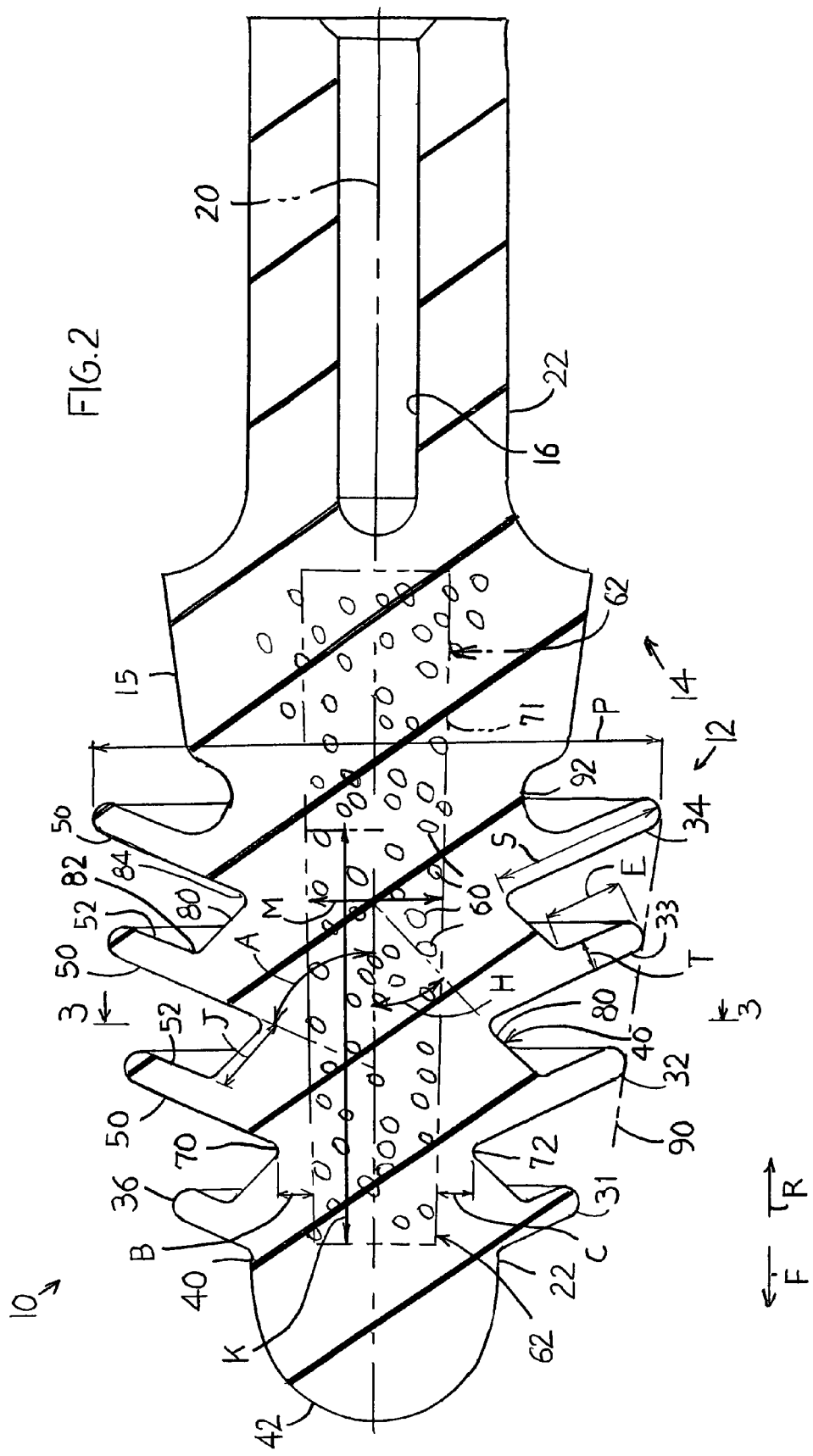

FIN EARPLUG

BACKGROUND OF THE INVENTION

Two major types of earplugs in widespread use are earplugs with bodies of elastomeric foam, and earplugs that are of nonfoam elastomeric material and that have flanges, or fins. Foam earplugs are formed of an elastomer with more than 25% of the volume being gas bubbles, and actually with more than 50% of the volume consisting of gas bubbles. Such foam earplugs are usually disposable in that they are commonly discarded by factory workers after each use.

One example of a nonfoam earplug with fins, shown in U.S. Pat. No. 6,241,041, has long and thin fins extending at rearward and radially-outward inclines from a stem portion or stem. Such finned earplugs generally do not block sound as well as foam earplugs, but the finned earplugs are reusable in that they stand wear and can be used many times. The noise blocking ability of an earplug is usually defined by its NRR number (noise reduction rating) according to a rating system established by the EPA (Environmental Protection Agency) of the United States. A finned nonfoam earplug of the type described in U.S. Pat. No. 6,241,041 has an NRR rating of 22 to 24. A foam earplug of the type described in U.S. Pat. No. 4,774,938 has an NRR rating of 34. It would be desirable if a finned nonfoam earplug had a higher NRR rating.

SUMMARY OF THE INVENTION

In accordance with one embodiment of the present invention, an earplug is provided that has fins and is constructed of nonfoam material, that has features that provide especially high noise attenuation in a comfortable earplug. The earplug is of the type that has a stem portion, or stem, and that has a plurality of fins that extend largely radially and at a rearward incline from the stem. The stem has a multiplicity of air pockets lying within an imaginary band that is centered on the earplug axis as seen in a sectional view taken along the axis, with the band having opposite sides spaced inward of the periphery of the stem so the air pockets do not open to the outside surface of the earplug. The air pockets have an area less than half, and actually less than one-quarter of the area of the earplug within the band, with solid material (no air pockets) occupying a majority of the band area, as seen in a sectional view taken along the earplug axis.

The fins are of constant thickness and are stubby, with a largely radial length that is no more than 5 times the average thickness of the fin. The stem periphery has peripheral stem parts extending between adjacent fins, and with each peripheral stem part extending at a constant rearward and radially-inward incline between the rear surface of one fin and the front surface of the next fin.

The novel features of the invention are set forth with particularity in the appended claims. The invention will be best understood from the following description when read in conjunction with the accompanying drawings.

BRIEF DESCRIPTION OF THE DRAWINGS

FIG. 2 is a sectional view of the earplug of FIG. 1, taken along the axis of the earplug.

DESCRIPTION OF THE PREFERRED EMBODIMENTS

Figure 1:
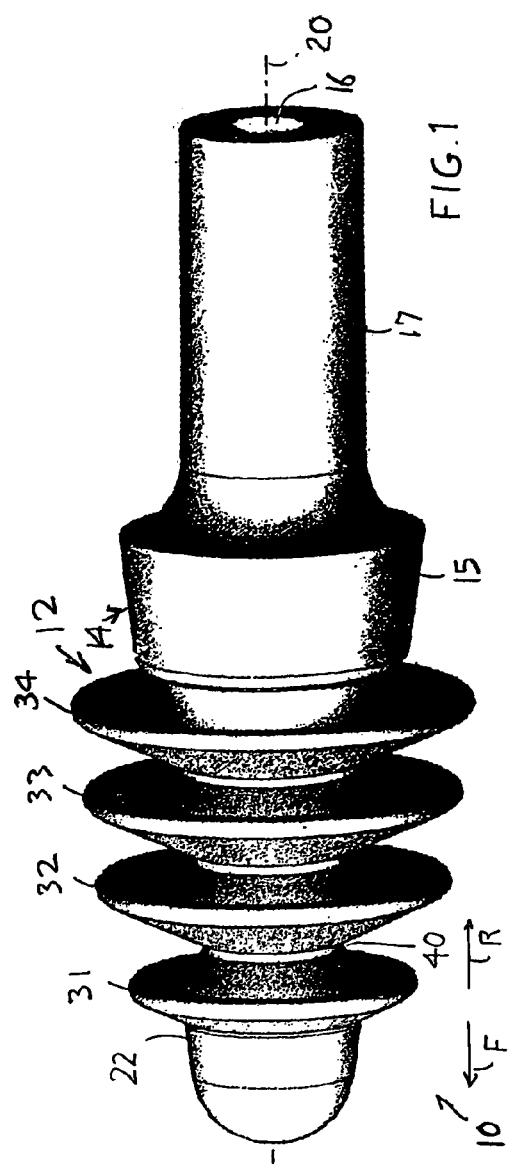
FIG. 1 is a rear isometric view of an earplug of the present invention.

FIG. 1 shows an earplug 10 of the invention, which includes a front portion 12 for insertion at least partially into a person's ear canal. The earplug also has a rear portion 14 with a base 15 and rear extension 17 that serve as a handle that can be held to insert and remove the earplug front portion from the person's ear. The particular earplug illustrated, has a passage 16 in its rear portion for holding an end of a cord that ties two earplugs together. The earplug has an axis 20 that extends in forward F and rearward R directions. The earplug includes a stem 22 that lies on the axis, and also includes a plurality of flanges or fins 31-34 that extend largely radially-outward (away from the axis) from the outside or periphery 40 of the stem.

FIG. 2 shows that the earplug has a rounded front end nose 42 forward of the fins, and the rear portion forms the base 15 rearward of the fins. Each of the fins has front and rear surfaces 50, 52 that are within 10° of parallel to each other and that extend at a rearward and radially-outward incline angle A of about 65° to the axis.

The earplug is molded of an elastomeric polymer, or elastomer, with a softness of about 25 to 30 on the Shore A scale. The material is nonfoam. A common foam earplug has gas (usually air) filled cells of an average diameter of about 0.1 mm to 0.2 mm. The gas-filled cells of a foam earplug occupy much more than 25% of the cross-sectional area of a foam earplug, and actually more than 50% of the cross-sectional area of a foam earplug, and there are small gas-filled cells even at the periphery of a foam earplug (unless a separate coating is applied around the foam). The nonfoam material of the earplug 10 of this invention has gas (air) filled cells 60 of slightly greater diameter (0.2 mm to 0.4 mm) than those of foam of common foam earplugs. However, the gas filled cells 60 of the earplug 10 of the invention occupy a total of less than 50% and actually less than 25% of the cross-sectional area of the earplug as taken on the axis, as shown in FIG. 2.

Figure 3:
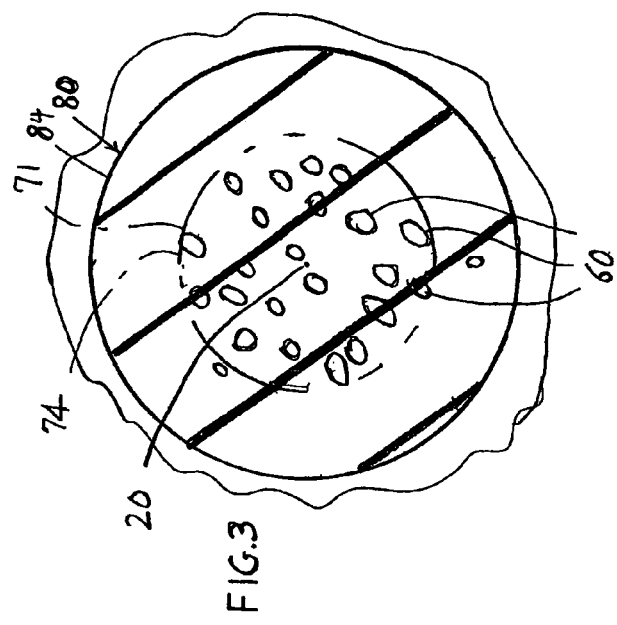
FIG. 3 is a sectional view taken perpendicular to the earplug along line 3-3 of FIG. 2.

The cells 60 of the nonfoam earplug 10 lie almost totally within a slightly tapered band-shaped imaginary area 62, when viewed in the sectional view taken on the axis of FIG. 2. The band-shaped area 62 lies on the earplug axis 20, and has opposite sides 64, 66 that are spaced a distance B, C from a corresponding side 70, 72 of the smallest diameter locations on the stem periphery (40). The spacings B and C are each a minimum of 0.1 mm and preferably a minimum of 0.2 mm. The total area of cells outside the area of the band 62 is less than 10% of the polymer-filled area outside the band and the percent of area occupied by cells outside the band is less than half the area occupied by cells in the band area. That is, the density of air pockets (the average percent of earplug cross-sectional area occupied by an air pocket, as seen in the sectional view of FIG. 3) is greater adjacent to the axis than adjacent to the surface, or periphery, of the stem, and the density of air pockets is more than twice as great within the band-shaped area 62 as outside the band-shaped area. Applicant is using the definition of "density" as the distribution of a quantity per unit area or volume. FIG. 3 shows that in a sectional view taken perpendicular to the axis, the cells 60 lie primarily within an area or region that lies in a circle 74 spaced from the periphery of the stem. Over 90% of the volume of the air pockets lies within a pocketed region 71 that lies a distance radially inwardly from the corner 84 of the stem peripheral parts 80 that is closest to the axis. The density of gas cells is much lower in a surrounding region that lies between the pocketed region 71 and the periphery of the stem such as at 84 than in the pocketed region 71. The band 62

(FIG. 2) has a length K forward of the rearmost flange 34 which is greater than the average band diameter M and is more than twice the band diameter.

The presence of the cells 60 reduces the passage of sound though the stem. When sound passing though a polymer encounters a gas pocket, some of the sound is attenuated by reflecting off the air-polymer interface. This helps account for the high noise blocking effect of foam. However, the lower percent of area occupied by the cells 60 in applicant's earplug results in little reduction of strength of the earplug stem so the earplug 10 can be used in the same manner as other prior nonfoam and finned earplugs.

Applicant creates the air pockets 60 by adding a foaming agent (about 5% of the polymer used in an injection molding). The polymer without foaming agent has a tendency to flow along the walls of the mold cavity, so the later addition of a separate foaming agent results in gas-filled cells that occupy the middle of the earplug and are spaced from the periphery and from the front end of the molded earplug.

The fins 31-34 have hemisphere rounded outer ends 36 and are each stubby, with a primarily uniform thickness T (the thickness T does not vary by more than 20% of the fin average thickness). The thickness T is at least 20% and preferably 30% (for fins 31-33) of the largely radial length E of the fin along the rear surface of the fin. This relatively large thickness T results in additional sound being blocked that otherwise would pass though the fins. It is well known that at least one fin, and preferably a plurality of fins should seal against the walls of the wearer's ear canal. However, engineers previously paid little attention to the passage of sound through the earplug material. Applicant's provision of air pockets in the stem and thick fins, reduces such sound passage. The front surface 50 of each fin has a length S that is more than 20% and preferably more than 33% greater than the length E of the rear surface 52 of the same fin.

Each of three stem periphery parts 80, which each is a part that lies between adjacent fins, extends continuously at a rearward and radially-inwardly incline angle H of more than 15°. Each of such three stem periphery parts extends from the rear face 52 of one fin to the front face 50 of the next adjacent and more rearward fin. The angle H is between 30° and 60°, and the actual incline angle H of the stem peripheral part 80 is about 43°. The corners 82, 84 where a stem peripheral part intersects the radially inner ends of the fin surfaces 50 and 52 have small radii of curvature, which are less than 10% of the distance J between the centers of the corners. The angle at the radially innermost corner 84 of a stem peripheral part is no more than 90° and is actually 70°. Applicant has experimented with different shapes of earplugs and found that the above described parameters each resulted in a greater NRR numbers and/or greater flexibility and comfort. For example, the use of the stem peripheral part 80 of the above construction and the sharp (small radius of curvature) corners resulted in greater flexibility and comfort to the wearer, and the overall changes resulted in an NRR number that increased from 22 or 24 to 26.

The earplug 10 is symmetric about the axis 20. Applicant has constructed and tested earplugs of the illustrated construction. The earplug largest fin has a diameter P of 12 mm. The three rearmost flanges 32-34 have outer ends that lie on a line 90 that is angled by 8° from the axis. The rear surface of the rearmost flange 34 merges with a stem peripheral part 92 that is rounded in about a half circle, all as seen in the sectional view taken along the axis 20 as in FIG. 2.

Thus, the invention provides an earplug body of the type that is formed of nonfoam polymer (less than 15% of the volume is occupied by gas-filled cells) and that has fins, which blocks a high percent of noise from reaching the wearer's ear drum for a nonfoam finned earplug, as specified by the NRR number, and that is comfortable to the wearer. The earplug includes a multiplicity (at least seven) of air pockets that are spaced from the periphery of the stem and from the fins. Over 90% of the air pocket volume lies in the imaginary cylindrical pocketed region 62, 74. The fins are of substantially uniform thickness and are stubby, with a largely radial length along a fin front surface which is no more than five times the fin thickness. The stem has stem peripheral parts each lying between the rear surface of one fin and the front surface of an adjacent fin. Each stem peripheral part extends at a rearward and radially-inward angle of more than 15° with respect to the earplug axis.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug with an integrally molded front portion for insertion at least partially into the ear canal of a person, said front portion being formed of nonfoam elastomeric material and having a stem with a stem outer surface or periphery, said stem extending along an earplug axis and said front portion having at least one 360° fin extending at least partially radially outward from said stem to engage walls of the person's ear canal, as seen in a sectional view taken along said axis, wherein:

said stem has a multiplicity of air pockets with the density of said air pockets being greater adjacent to the earplug axis than adjacent to a periphery of said stem, to thereby reduce the passage of sound through the stem.

2. The earplug described in claim 1 wherein:

said stem has a periphery;

over 90% of the volume of said air pockets lie in a pocketed region that is centered on said axis, that is elongated along said axis, and that has a periphery spaced radially inward of said stem periphery.

3. An earplug with a front portion for forward insertion at least partially into the ear canal of a person, said front portion being formed of elastomeric material, said front portion having a stem extending along an earplug axis and having a plurality of fins each extending 360° about said axis, said fins being spaced apart along said axis, the plurality of said fins each has front and rear surfaces that each extends at a rearward and radially outward incline as seen in a sectional view taken perpendicular to said axis, and said stem having a peripheral part lying between each pair of two adjacent fins of said plurality of fins, wherein:

each of said plurality of fins has front and rear surfaces that extend within 10° of parallel to each other as seen in said sectional view, and the front surface of each of said plurality of fins has a length (S) longer than the length (E) of the rear surface of the same fins;

said stem peripheral part extending at a rearward and radially inward incline of more than 15° to said axis, all along said stem peripheral part.

4. An earplug with an integrally molded front portion for insertion at least partially into the ear canal of a person, said front portion being formed of elastomeric material and having a stem extending along an earplug axis and having at least one 360° fin extending at least partially radially outward from said stem to engage walls of the person's ear canal, wherein:

said stem has a periphery that is furthest from said axis and said stem has a multiplicity of gas cells that lie in a high density in a region (62) that is centered on said axis and that is spaced radially inward from said periphery of said stem, with a surrounding region of said stem that extends between said pocketed region and said stem periphery having less than half said high density of gas cells, with both said regions being integrally molded.

5. The earplug described in claim 4, wherein:
over 90% of the volume of said gas cells lie in said pocketed region.

6. An earplug with an integrally molded front portion for insertion at least partially into the ear canal of a person, said front portion being formed of nonfoam elastomeric material and having a stem with a stem outer surface or periphery, said stem extending along an earplug axis and said front portion having a plurality of fins including first and second adjacent 360° fins each extending at least partially radially outward from said stem to engage walls of the person's ear canal, as seen in a sectional view taken perpendicular to said axis, wherein:

said stem has a multiplicity of air pockets with the density of said air pockets being greater adjacent to the earplug axis than adjacent to a periphery of said stem, to thereby reduce the passage of sound through the stem, and including a foamed foaming agent lying at a higher density adjacent to said earplug axis than adjacent to said periphery of said stem;

said first and second fins each extends at a primarily constant radially outward and rearward incline to said earplug axis, said first fin lying forward of said second fin and said first fin has a rear surface (52) that faces a front surface (50) of said second fin, and said stem portion has a stem peripheral part (80) extending between radially inner ends of said first and second fins;

said stem peripheral part extends continuously at a rearward and radially inward incline of more than 15° to said axis, all the way from the radially inner end of said first fin rear surface to the radially inner end of said second fin front surface;

said second fin front surface extends at a forward and radially inward angle (A) of more than 50° to said axis, and the angle between said stem peripheral part (80) and said second fin front surface (50) is no more than 90°.

7. An earplug with an integrally molded front portion for insertion at least partially into the ear canal of a person, said front portion being formed of nonfoam elastomeric material and having a stem with a stem outer surface or periphery, said stem extending along an earplug axis and said front portion having at least one 360° fin extending at least partially radially outward from said stem to engage walls of the person's ear canal, as seen in a sectional view taken along said axis, said front portion having a front end forming a rounded nose (42) for entering an ear canal, said at least one fin includes a plurality of fins including first and second adjacent fins that each extends at a primarily constant radially outward and rearward incline to said earplug axis, said first fin lying forward of said second fin and said first fin has a rear surface (52) that faces a front surface (50) of said second fin, and said stem has a stem peripheral part (80) extending between radially inner ends of said first and second fins, wherein:

said stem has a multiplicity of air pockets with the density of said air pockets being greater adjacent to the earplug axis than adjacent to a periphery of said stem, to thereby reduce the passage of sound through the stem;

said stem peripheral part extends continuously at a rearward and radially inward incline of more than 15° to said axis, all the way from the radially inner end of said first fin rear surface to the radially inner end of said second fin front surface.

\* \* \* \* \*

UNITED STATES PATENT AND TRADEMARK OFFICE
CERTIFICATE OF CORRECTION

PATENT NO. : 8,479,744 B2  
APPLICATION NO. : 11/144514  
DATED : July 9, 2013  
INVENTOR(S) : Thomas W. Fleming Page 1 of 1

It is certified that error appears in the above-identified patent and that said Letters Patent is hereby corrected as shown below:

On the Title page, Item (73) Assignee: replace "Sperlan" with --Sperian--

Signed and Sealed this  
Twenty-fourth Day of September, 2013

Teresa Stanek Rea  
*Deputy Director of the United States Patent and Trademark Office*